United States Patent [19]
Leban

[11] Patent Number: 5,944,719
[45] Date of Patent: Aug. 31, 1999

[54] EXTERNAL FIXATOR

[75] Inventor: Stanley Leban, Islandia, N.Y.

[73] Assignee: Millennium Devices, L.L.C., Islandia, N.Y.

[21] Appl. No.: 09/189,018

[22] Filed: Nov. 10, 1998

[51] Int. Cl.⁶ .................................................. A61B 17/60
[52] U.S. Cl. .............................................. 606/59; 606/54
[58] Field of Search .................................. 606/54, 55, 56, 606/57, 58, 59, 53, 60, 61, 72, 73

[56] References Cited

U.S. PATENT DOCUMENTS

| | | |
|---|---|---|
| 4,714,076 | 12/1987 | Comte . |
| 4,745,913 | 5/1988 | Castaman . |
| 5,019,077 | 5/1991 | De Bastiani . |
| 5,320,622 | 6/1994 | Faccioli . |
| 5,649,925 | 7/1997 | Alacreu ...................................... 606/61 |
| 5,788,695 | 8/1998 | Richardson . |

Primary Examiner—Guy V. Tucker
Attorney, Agent, or Firm—Collard & Roe, P.C.

[57] ABSTRACT

An external fixator for setting fractured bones, comprising a flexible, articulable column comprised of a series of ball and socket members linked by a tensioning cable threaded therethrough. Tightening the cable forces the ball and socket members together and makes the column rigid. There is a mechanism for tightening the cable and keeping the cable in a tightened position to allow the bones to set without moving. A plurality of pivotable pin holders are arranged along the column for attaching to pins inserted into the fractured bones, thus attaching the column to the bones to be set. There is also a mechanism for fixing each pin holder into a rigid position so that there can be no pivoting motion after the proper position of the fixator has been achieved. The external fixator according to the invention has the advantage of added flexibility during positioning of the fixator onto the fractured bones, while being able to obtain the necessary rigidity for proper bone setting.

6 Claims, 4 Drawing Sheets

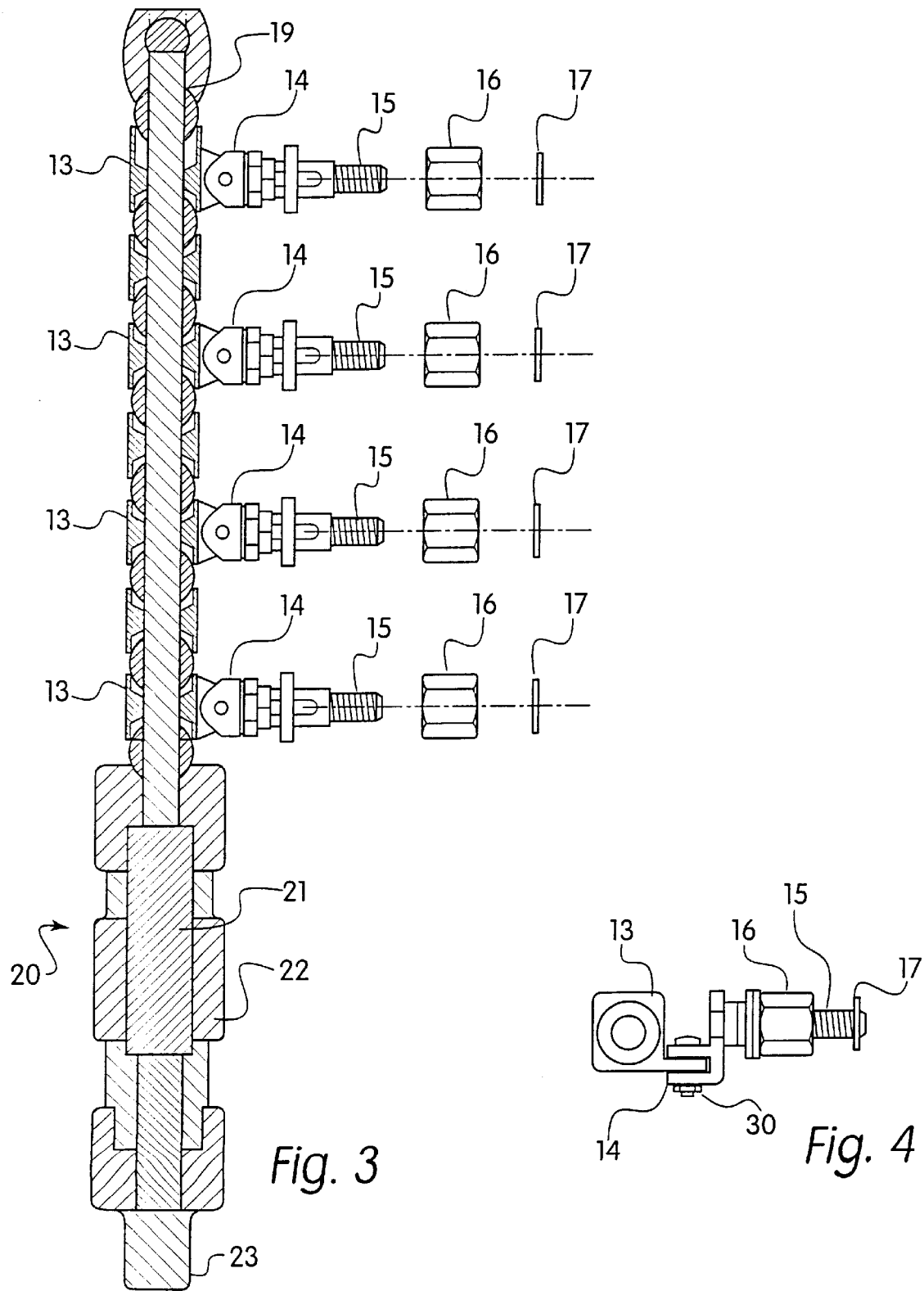

EXTERNAL FIXATOR

BACKGROUND OF THE INVENTION

1. Field of the Invention

This invention relates to an external fixator for repairing fractured bones. In particular, the invention relates to a fixator having a flexible spine that can be tightened and made rigid after the fixator is attached to the bones.

2. The Prior Art

Fractured bones are often set with external fixating devices. These devices comprise a plurality of pins or screws that are inserted into the fractured bones, and which are then attached to a pin holder, which fixes the bones in a stationary position. Many pin holders consist of rigid arms that may or may not be pivotable at selected points. One such device is disclosed in U.S. Pat. No. 4,714,076 to Comte et al. This device shows two segments of a pin holder that are pivotally connected to a central connecting device. Another such device is shown in U.S. Pat. No. 4,745,913 to Castaman et al, which shows two rigid pin holders that are pivotally connected to each other.

Various other splints are shown in U.S. Pat. Nos. 5,019,077 to DeBastiani et al., 5,320,622 to Faccioli et al., and 5,788,695 to Richardson et al. While all of these devices are capable of setting bones, they suffer from the drawback that the pin holders are not adjustable enough to obtain the best positioning for setting the bones.

SUMMARY OF THE INVENTION

It is therefore an object of the present invention to provide an external fixator that is flexible throughout its length.

It is another object of the present invention to provide an external fixator that can be made rigid after the precise settings have been made, to keep the bones in place.

It is yet another object of the present invention to provide an external fixator that is adapted for use on a large variety of fractures.

It is a further object of the present invention to provide an external fixator that is simple to manufacture and use.

These and other objects are achieved by an external fixator for setting fractured bones, comprising a flexible, articulable column comprised of a series of ball and socket members linked by a tensioning cable threaded therethrough. Tightening the cable forces the ball and socket members together and makes the column rigid. There are means for tightening the cable and keeping the cable in a tightened position to allow the bones to set without moving.

A plurality of pivotable pin holders are arranged along the column for attaching to pins inserted into the fractured bones, thus attaching the column to the bones to be set. There is also means for fixing each pin holder into a rigid position so that there can be no pivoting motion after the proper position of the fixator has been achieved.

The external fixator according to the invention has the advantage of added flexibility during positioning of the fixator onto the fractured bones, while being able to obtain the necessary rigidity for proper bone setting. This is because the column and pin holders are entirely flexible and movable during positioning of the fixator, but are tightened to become completely rigid after the desired positioning has been achieved.

The pin holders are comprised of a hinged portion connected to the column, a hollow portion for receiving the pin, a threaded tip and a nut for mounting on the threaded tip for keeping a pin inserted into the pin holder. A pin is inserted into the threaded tip and the nut is tightened around the pin and threaded tip until the pin is secured firmly into the pin holder. At this point the pin holder can still pivot. However, at the point where rigidity is desired, the pin holder can be tightened via an allen screw on the hinged portion that can be tightened to prevent further pivoting of the pin holder. The hinged portion of the pin holder is preferably connected to a collar surrounding the column which provides a pivot point for the pin holder.

The tensioning cable is tightened by a threaded draw bar connected at one end to the cable surrounded by a threaded body. Rotating the threaded body along the draw bar tightens the cable and makes the column rigid by pressing the ball and socket members against each other until no play is left.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 3 shows a partial cross-sectional view of the fixator according to the invention with the pin holder assembly in an exploded view;

FIG. 4 shows a top view of the pin holder assembly as assembled;

DETAILED DESCRIPTION OF THE PREFERRED EMBODIMENT

Figure 1:
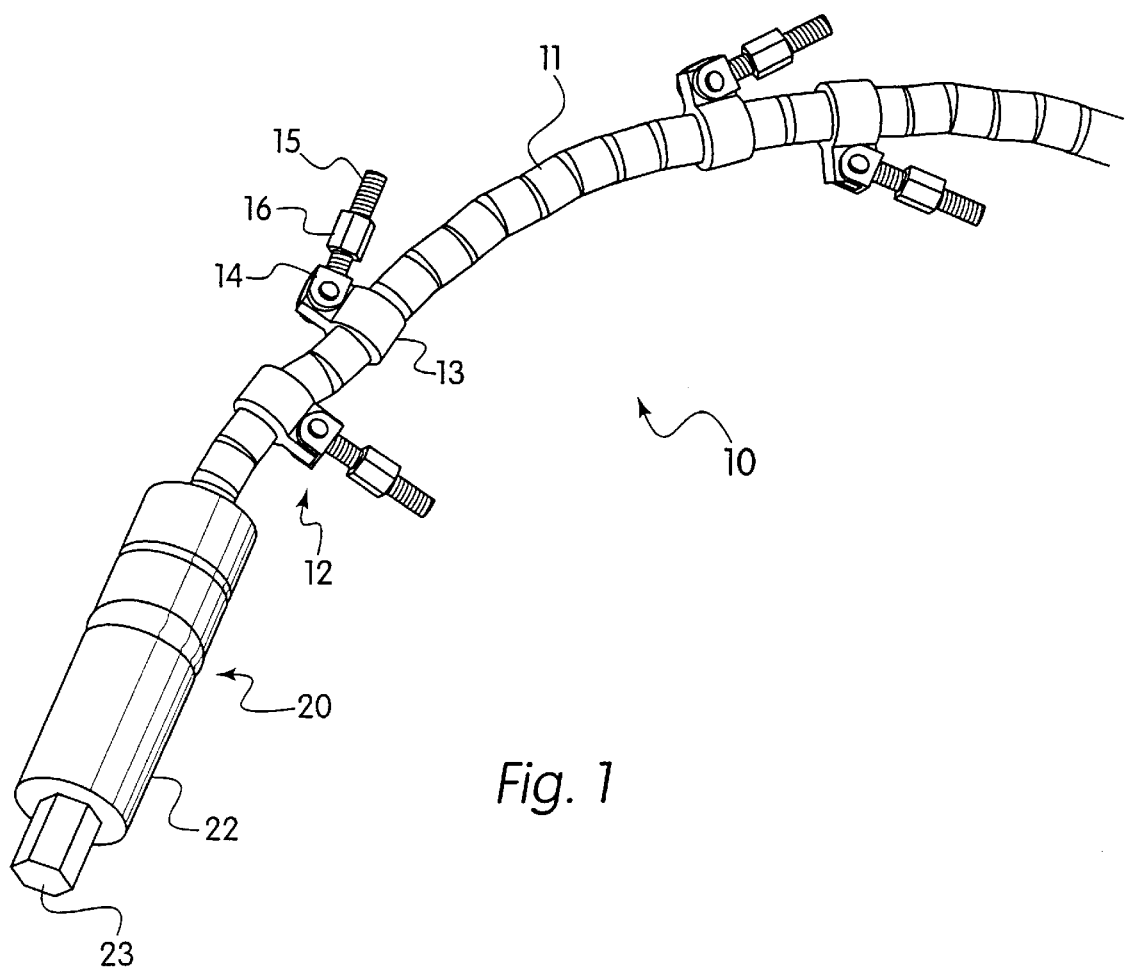
FIG. 1 shows a perspective view of the fixator according to the invention.
Figure 2:
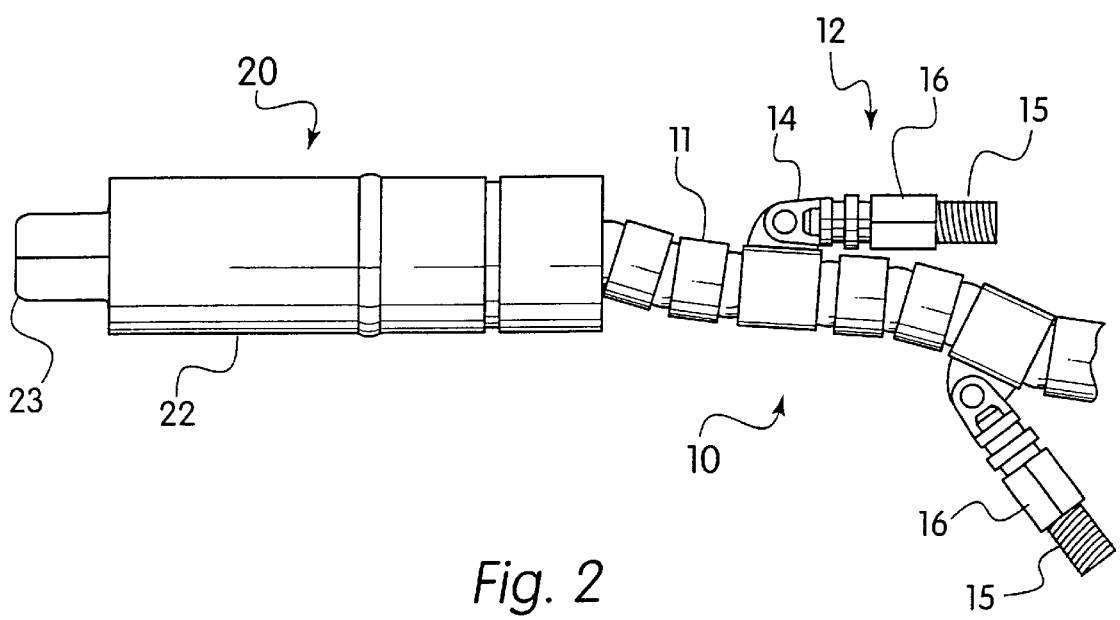
FIG. 2 shows an enlarged view of one end of the fixator shown in FIG. 2.

Referring now in detail to the drawings and, in particular, FIGS. 1 and 2 show the fixator 10 according to the invention. Fixator 10 comprises a flexible column 11 made of stacked ball and socket components such as that disclosed in U.S. Pat. No. 4,949,927.

A plurality of pin holders 12 are arranged at selected places along column 11 for engaging pins inserted in fractured bones. Each pin holder 12 comprises a collar 13 mounted around column 11, a hinged portion 14, a threaded hollow end 15 for receiving the pin, and a retainer nut 16 for securing the pin in pin holder 11. A washer 17 is also placed on end 15 for securing the bone pins.

As shown in FIG. 3, a cable 19 is threaded through column 11 and extends from the top of the column to a draw bar assembly 20 located at the other end of column 11. As fixator 10 is being positioned on the fractured bones, cable 19 is slack and column 11 is flexible to allow precise positioning of column 11. When the desired positioning has been attained, cable 19 is tightened via draw bar assembly 20 to make column 11 completely rigid.

Draw bar assembly 20 is comprised of an externally threaded draw bar 21 connected to cable 19. An internally threaded housing 22 surrounds draw bar 21. Cable 19 is tightened by rotating housing 22, causing it to move up the threads of draw bar 21 until housing 22 abuts column 11 and cannot be rotated further. At this point, column 11 becomes rigid because all of the ball and socket elements are pressed together with no room for play. The end 23 of housing 22 is hexagonally shaped so that housing 22 can be easily rotated by a hex wrench.

As shown in FIG. 4, hinged portion 14 of pin holder 12 has a screw 20 through the hinge. Screw 20 can be tightened to secure pin holder 12 in a fixed position after fixator 10 has been mounted to the fractured bones and the desired positioning of fixator 10 has been achieved.

Figure 5:
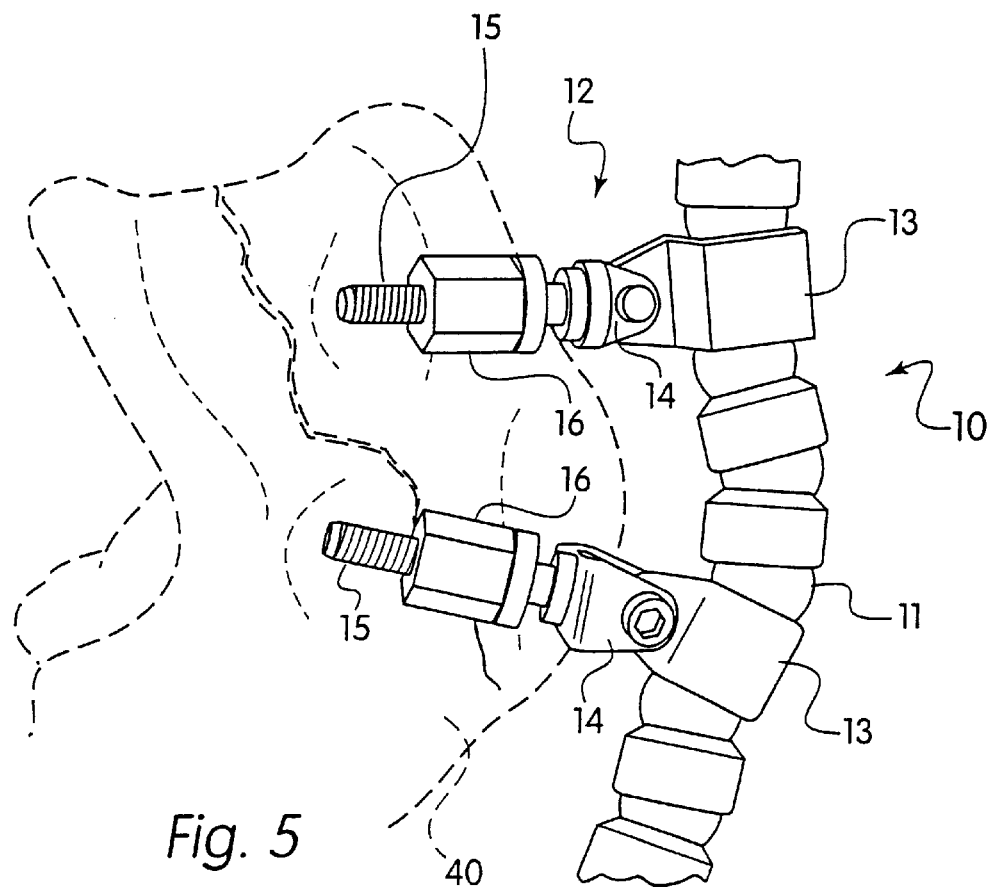
FIG. 5 shows a perspective view of the fixator as mounted to a fractured bone.
Figure 6:
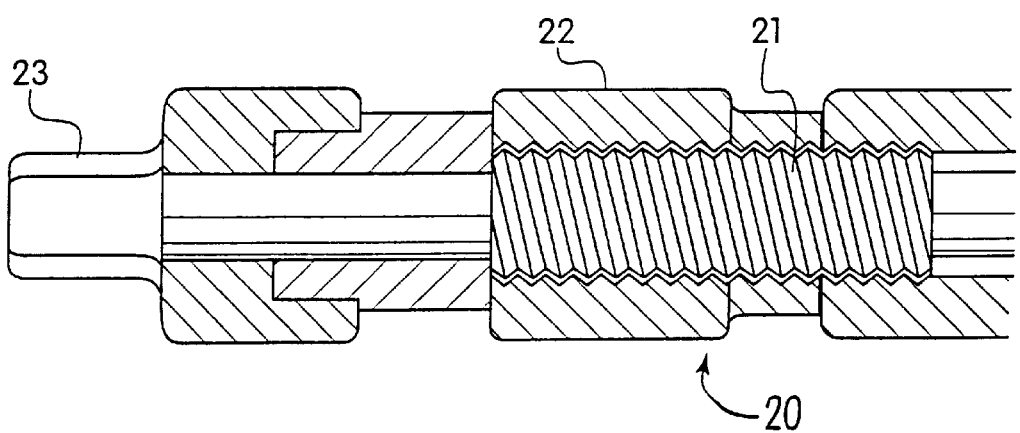
FIG. 6 shows a cross-sectional view of the draw bar assembly on the fixator according to the invention.

The use of fixator 10 to fix fractured bones is shown in FIG. 5. Here, pin holders 12 are attached to pins (not shown) that are inserted into the fractured bone 40. Fixator 10 stays in place until the desired healing has been accomplished.

The device allows the clinician to place pins in any arrangement or configuration, since the fixator is infinitely adjustable and capable of engaging them into a rigid framework Accordingly, while only a single embodiment of the present invention has been shown and described, it is obvious that many changes and modifications may be made thereunto without departing from the spirit and scope of the invention.

What is claimed is:

1. A device for setting fractured bones, comprising:

a flexible, articulable column comprised of a series of ball and socket members;

a tensioning cable strung through the column such that tightening the cable forces the ball and socket members together and makes the column rigid;

means for tightening the cable and keeping the cable in a tightened position;

a plurality of pivotable pin holders arranged along the column for attaching to pins inserted into the fractured bones; and means for fixing each pin holder into a rigid position.

2. The device according to claim 1, wherein the pin holders are comprised of a hinged portion connected to the column, a hollow portion for receiving the pin, a threaded tip and a nut for mounting on the threaded tip for keeping a pin inserted into the pin holder.

3. The device according to claim 2, wherein the means for fixing each pin holder into a rigid position comprises a bolt extending through the hinged portion, said bolt adapted to be tightened to fix the pin holder into a rigid position.

4. The device according to claim 2, further comprising a plurality of collars surrounding the column, each collar connected the hinged portion of one of the pin holders.

5. The device according to claim 1, wherein the means for tightening the tensioning cable comprises an externally threaded draw bar connected to the cable at one end, and an internally threaded body surrounding the draw bar, wherein rotating the threaded body along the draw bar tightens the cable and makes the column rigid.

6. The device according to claim 5, wherein the threaded body has a hexagonally shaped end portion.

\* \* \* \* \*